United States Patent (10) Patent No.: US 9,339,648 B2
Smith (45) Date of Patent: *May 17, 2016

(54) STIMULUS TIMING FOR A STIMULATING MEDICAL DEVICE

(71) Applicant: Cochlear Limited, Macquarie University, NSW (AU)

(72) Inventor: Zachary Mark Smith, Englewood, CO (US)

(73) Assignee: Cochlear Limited, Macquarie University, NSW (AU)

(*) Notice: Subject to any disclaimer, the term of this patent is extended or adjusted under 35 U.S.C. 154(b) by 66 days.

This patent is subject to a terminal disclaimer.

(21) Appl. No.: 14/165,936

(22) Filed: Jan. 28, 2014

(65) Prior Publication Data

US 2014/0222104 A1 Aug. 7, 2014

Related U.S. Application Data

(63) Continuation of application No. 12/366,462, filed on Feb. 5, 2009, now Pat. No. 8,688,222.

(51) Int. Cl.
*A61N 1/36* (2006.01)
*H04R 25/00* (2006.01)

(52) U.S. Cl.
CPC .......... *A61N 1/36032* (2013.01); *H04R 25/505* (2013.01)

(58) Field of Classification Search
CPC ............. A61N 1/36032; H04R 25/505; H04R 25/606; H04R 2225/67
See application file for complete search history.

(56) References Cited

U.S. PATENT DOCUMENTS

| | | |
|---|---|---|
| 3,563,246 A | 2/1971 | Puharich et al. |
| 4,532,930 A | 8/1985 | Crosby et al. |
| 4,592,359 A | 6/1986 | Galbraith |
| 4,640,286 A | 2/1987 | Thomson |
| 4,735,204 A | 4/1988 | Sussman et al. |
| 5,271,397 A | 12/1993 | Seligman et al. |
| 5,735,887 A | 4/1998 | Barreras |

(Continued)

FOREIGN PATENT DOCUMENTS

| | | |
|---|---|---|
| CN | 102740926 | 10/2012 |
| FR | 2690550 | 10/1993 |

(Continued)

OTHER PUBLICATIONS

Office Action in Chinese Application No. 201080015175.X, mailed Apr. 1, 2014, 35 pages.

(Continued)

*Primary Examiner* — Catherine Voorhees

(57) ABSTRACT

Methods and systems are disclosed for determining the timing of stimulation applied using a medical device. In embodiments, the medical device filters a received signal to obtain a plurality of band-pass filtered signals, each corresponding to one or more stimulation channels. The medical device then determines the envelopes of these band-pass filtered signals. Next, the medical device determines the stimulation timing (i.e., the pulse times) for the corresponding stimulation channel based on the timing of a particular phase (e.g., a peak, a minimum, etc.) of the envelope. A pulse amplitude for the stimulation channel may then be determined, and stimulation applied using the determined amplitude and pulse time.

15 Claims, 5 Drawing Sheets

(56) References Cited

U.S. PATENT DOCUMENTS

| | | | |
|---|---|---|---|
| 6,078,838 | A | 6/2000 | Rubinstein |
| 6,198,971 | B1 | 3/2001 | Leysieffer |
| 6,289,247 | B1 | 9/2001 | Faltys et al. |
| 6,295,472 | B1 | 9/2001 | Rubinstein et al. |
| 6,631,295 | B2 | 10/2003 | Rubinstein et al. |
| 6,845,271 | B2 | 1/2005 | Fang et al. |
| 7,072,717 | B1 | 7/2006 | Wolf et al. |
| 7,242,985 | B1 | 7/2007 | Fridman et al. |
| 7,310,558 | B2 | 12/2007 | Van Hoesel |
| 7,333,858 | B2 | 2/2008 | Killian |
| 7,574,264 | B2 | 8/2009 | Wolfe et al. |
| 8,688,222 | B2 * | 4/2014 | Smith ............... A61N 1/36032 607/2 |
| 2003/0114899 | A1 | 6/2003 | Woods et al. |
| 2004/0172101 | A1 | 9/2004 | Van Hoesel |
| 2006/0052841 | A1 * | 3/2006 | Daly .................. A61N 1/08 607/57 |
| 2006/0080087 | A1 | 4/2006 | Vandali et al. |
| 2008/0177354 | A1 | 7/2008 | Killian |
| 2009/0018609 | A1 | 1/2009 | Dilorenzo |
| 2009/0125082 | A1 | 5/2009 | Schleich |
| 2009/0177247 | A1 | 7/2009 | Neal et al. |
| 2011/0040352 | A1 | 2/2011 | Gerber et al. |

FOREIGN PATENT DOCUMENTS

| | | |
|---|---|---|
| WO | 99/49815 | 10/1999 |
| WO | 99/65276 A1 | 12/1999 |
| WO | 01/03622 A1 | 1/2001 |
| WO | 01/19304 | 3/2001 |
| WO | 01/99470 A1 | 12/2001 |
| WO | 02/17679 | 2/2002 |
| WO | 02/096153 A1 | 11/2002 |
| WO | 2010/091174 | 8/2010 |

OTHER PUBLICATIONS

Office Action in Chinese Application No. 201080015175.X, mailed Dec. 29, 2014, 39 pages.

Wilson et al., "Speech Recognition for Auditory Prostheses," NIH Contract N01-DC-9-2401, 3rd Quarterly Progress Report, Research Triangle Park: Neuroscience Program Office, Research Triangle Institute, Jan. 1990.

Wilson et al., "Better Speech Recognition with Cochlear Implants," Nature 352, pp. 236-238, Jul. 1991.

International Preliminary Examination Report for PCT/AU02/00660 dated Dec. 24, 2002, 3 pages.

International Search Report for PCT/AU02/00660 dated Sep. 3, 2002, 3 pages.

Sit et al., "A Low-Power Asynchronous Interleaved Sampling Algorithm for Cochlear Implants that Encodes Envelope and Phase Information," IEEE Trans. Biomed Eng., vol. 54, No. 1, pp. 138-149, Jan. 2007.

Office Action in Chinese Application No. 201080015175.X with English translation, mailed Jul. 10, 2015, 15 pages.

English translation of Office Action in counterpart Chinese Application No. 201080015175.X, mailed Jan. 5, 2016, 3 pages.

* cited by examiner

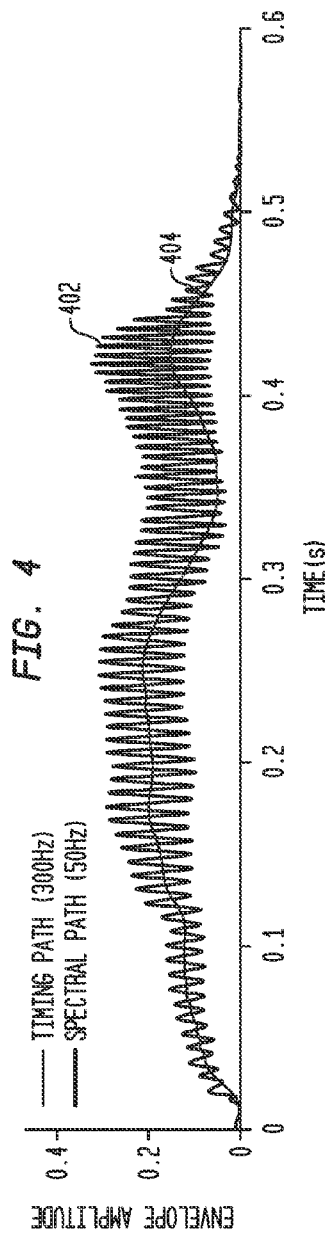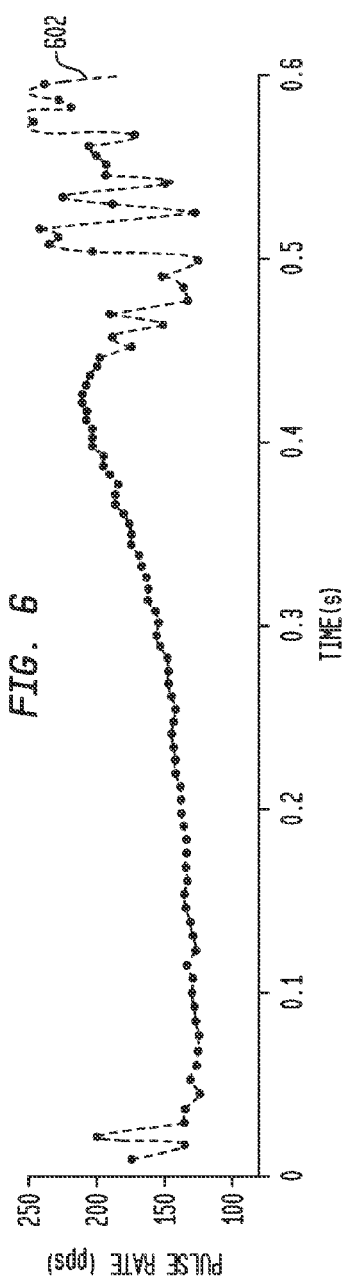
FIG. 4
FIG. 5
FIG. 6

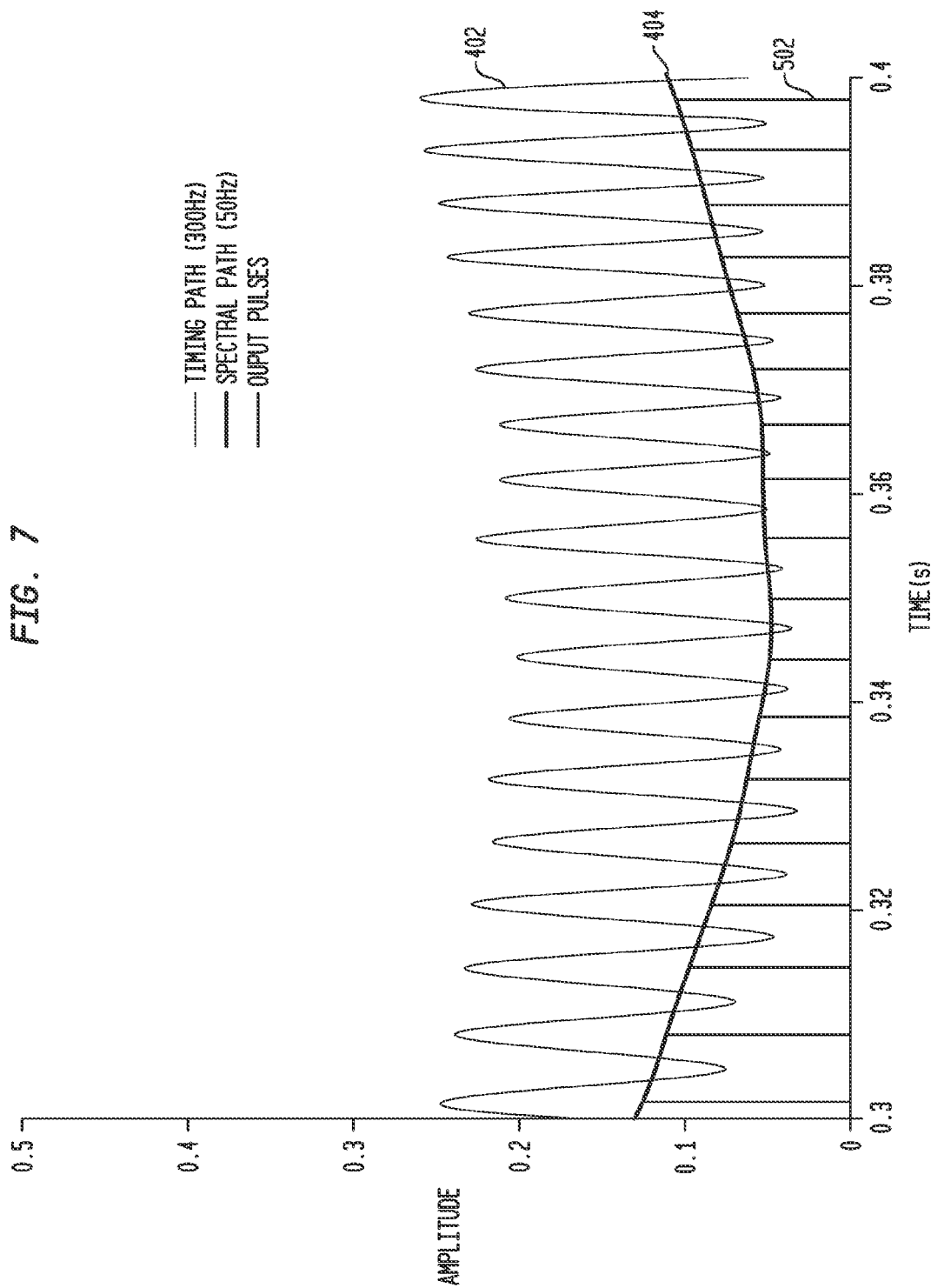

STIMULUS TIMING FOR A STIMULATING MEDICAL DEVICE

CROSS-REFERENCE TO RELATED APPLICATIONS

This application is a continuation of U.S. patent application Ser. No. 12/366,462, entitled "STIMULUS TIMING FOR A STIMULATING MEDICAL DEVICE," filed on Feb. 5, 2009, now U.S. Pat. No. 8,688,222 the entire contents and disclosures of which are hereby incorporated by reference herein.

BACKGROUND

1. Field of the Invention

The present invention relates generally to stimulating medical device, and more particularly, to stimulus timing in a stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of the recipient's auditory system have been developed to provide persons having sensorineural hearing loss with the ability to perceive sound. Such stimulating hearing prostheses include, for example, auditory brain stimulators and cochlear prostheses (commonly referred to as cochlear prosthetic devices, cochlear implants, cochlear devices, and the like, and will be referred to simply as "cochlear implants" herein.) As used herein, the recipient's auditory system includes all sensory system components used to perceive a sound signal, such as hearing sensation receptors, neural pathways, including the auditory nerve and spiral ganglion, and parts of the brain used to sense sounds.

Most sensorineural hearing loss is due to the absence or destruction of the cochlear hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential frequencies of sound.

Auditory brain stimulators are used to treat a smaller number of recipients with bilateral degeneration of the auditory nerve. For such recipients, the auditory brain stimulator provides stimulation of the cochlear nucleus in the brainstem.

In applying electrical stimulation to a recipient, medical devices, such as cochlear implants and auditory brain stimulators, typically use a coding strategy in determining the timing and intensity of the stimulation pulses to be applied. These coding strategies, however, often result in variable latency for received signals. That is, the amount of time taken for a signal being received until the time the corresponding stimulation signal is applied (i.e., used to stimulate the recipient) is variable. In bilateral devices (e.g., where a cochlear implant is used in both errors) this variable latency can result in the loss of phase difference information between signals received at the left and right ears (i.e., the difference in time between when a sound signal is received at one ear versus the other ear). This loss of information may result in poor coding of interaural timing cues for bilateral devices, as well as poor coding of the fundamental frequency for both speech and music. Additionally, typical cochlear implant systems use a fixed pulse rate for applying stimulation. This pulse rate is typically set to a high rate so that the perceived sound doesn't seem less natural and overly robotic to the recipient. This high fixed pulse rate however can result in large power requirements, which reduce the life of the medical devices battery and/or requires larger more powerful batteries. This adds cost, size, and/or inconvenience to the medical device.

SUMMARY

In one aspect of the present invention there is provided a method for delivering a stimulating signal by a stimulating medical device having a plurality of electrodes. This method comprises receiving a signal; filtering the received signal to obtain a first set of one or more band-pass filtered signals; determining a timing envelope by determining an envelope of at least one of the band-pass filtered signals; determining a pulse time based on when a phase of the timing envelope is equal to a specified phase; determining an amplitude for the pulse time; and delivering a stimulation signal using one or more of the plurality of electrodes using the determined pulse time and amplitude.

In another aspect there is provided an apparatus for use in delivering a stimulating signal by a stimulating medical device having a plurality of electrodes. This apparatus comprises a first set of one or more band-pass filters configured to filter a received signal to obtain a first set of one or more band-pass filtered signals; a first set of at least one envelope detector configured to determine a timing envelope by determining an envelope of at least one of the band-pass filtered signals; a first set of one or more pulse time selectors configured to determine a pulse time based on when a phase of the timing envelope is equal to a specified phase; a first set of one or more amplitude selectors configured to determine an amplitude for the pulse time; and a transmitter for transmitting the determined pulse time and amplitude for use in delivering a stimulation signal using one or more of the plurality of electrodes and using the determined pulse time and amplitude.

In yet another aspect there is provided a computer readable medium comprising a computer program for controlling a processor to execute a method for method for delivering a stimulating signal by a stimulating medical device having a plurality of electrodes. This method comprises receiving a signal; filtering the received signal to obtain a first set of one or more band-pass filtered signals; determining a timing envelope by determining an envelope of at least one of the band-pass filtered signals; determining a pulse time based on when a phase of the timing envelope is equal to a specified phase; determining an amplitude for the pulse time; and delivering a stimulation signal using one or more of the plurality of electrodes using the determined pulse time and amplitude.

In yet another aspect there is provided a system for delivering a stimulating signal by a stimulating medical device having a plurality of electrodes. This system comprises means for receiving a signal; means for filtering the received signal to obtain a first set of one or more band-pass filtered signals; means for determining a timing envelope by determining an envelope of at least one of the band-pass filtered signals; means for determining a pulse time based on when a phase of the timing envelope is equal to a specified phase; means for determining an amplitude for the pulse time; and means for delivering a stimulation signal using one or more of the plurality of electrodes using the determined pulse time and amplitude.

BRIEF DESCRIPTION OF THE DRAWINGS

Embodiments of the present invention are described below with reference to the attached drawings, in which:

FIG. 4 illustrates an exemplary timing signal for and an exemplary spectral signal, in accordance with an embodiment;

FIG. 5 illustrates exemplary combined output pulses resulting combining pulse times from a timing path with amplitudes from a spectral path, in accordance with an embodiment;

FIG. 6 illustrates the instantaneous pulse rate of the output pulses of FIG. 5, in accordance with an embodiment;

FIG. 7 illustrates a timing signal, spectral signal, and resulting output pulses, in accordance with an embodiment.

DETAILED DESCRIPTION

Figure 1:
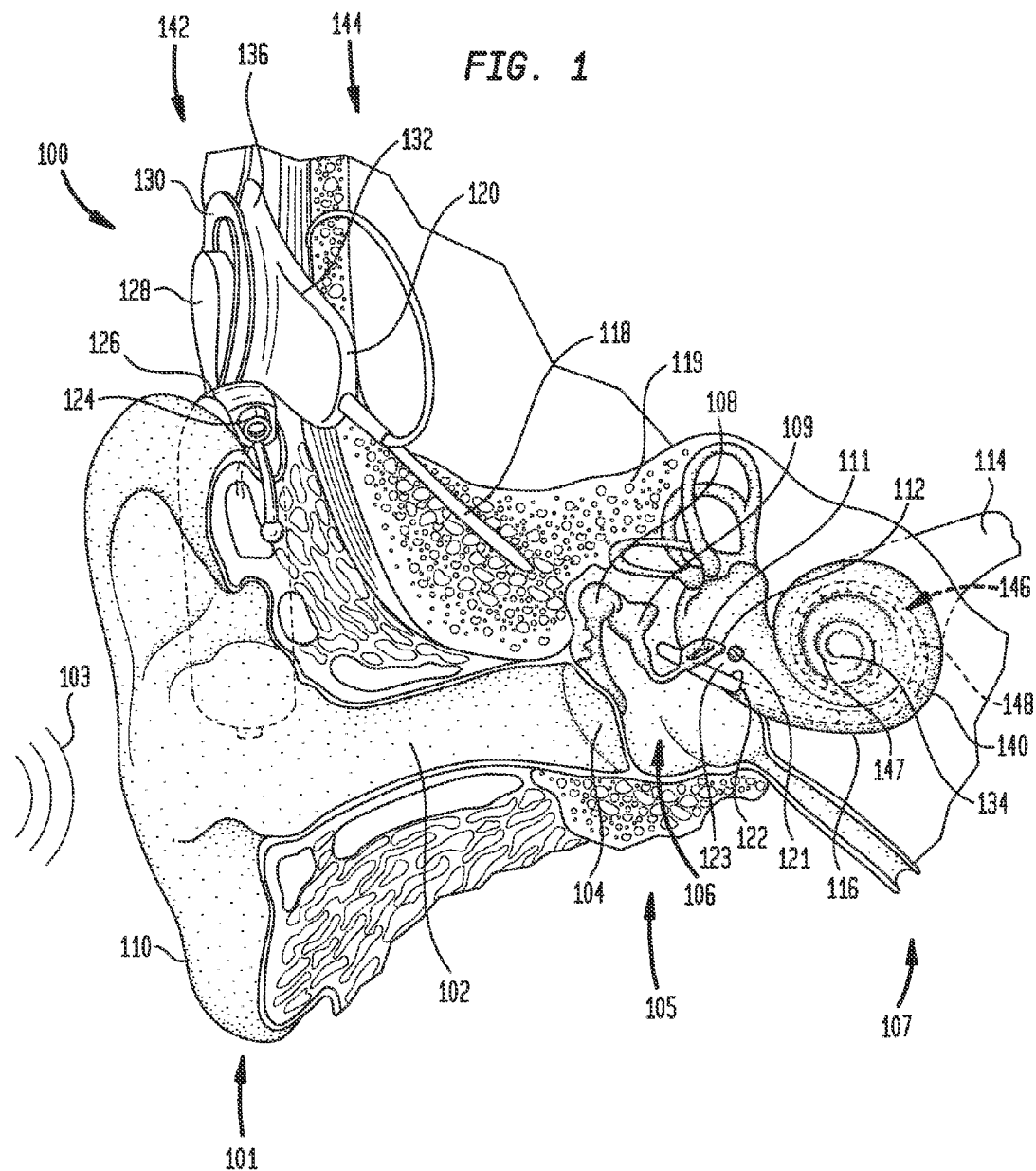
FIG. 1 is a perspective view of a cochlear implant in which embodiments of the present invention may be implemented.

Aspects of the present invention are generally directed to methods and systems for determining the timing of stimulation applied using a medical device, such as a cochlear implant or an auditory brain stimulator. In embodiments, the medical device filters a received signal to obtain a plurality of band-pass filtered signals, each corresponding to one or more stimulation channels. The medical device then determines the envelopes of these band-pass filtered signals. Next, the medical device determines the stimulation timing (i.e., the pulse times) for the corresponding stimulation channel based on the timing of a particular phase (e.g., a peak, a minimum, etc.) of the envelope. For example, the medical device may select the stimulation pulse times based on when the corresponding envelope reaches its peaks.

In an embodiment, the medical device may determine the stimulation timing using a mechanism in which the medical device processes the received signals using two separate and parallel processing paths. The first path provides the timing information for each of a plurality of different stimulation channels. As noted above, this timing information may include the times at which the medical device is to apply a stimulation pulse on the stimulation channel. The second path provides information regarding the intensity of the stimulation to be applied.

The first path may comprise a plurality of band-pass filters, each corresponding to a particular stimulation channel. Each of these band-pass filters outputs a signal that is provided to an envelope detector to obtain the envelope of the filtered signal. Next, a pulse time selector may be used to obtain the times at which the envelope reaches its peaks, or another particular phase of the envelope signal. These peak times provide the pulse times for each of the corresponding stimulation channels.

The second processing path may also comprise a plurality of band-pass filters followed by a corresponding envelope detector that outputs the envelope for the filtered signal. The medical device may then determine for each pulse from the first path, the amplitude of the envelope at the corresponding time and channel from the second path. The medical device may then combine the pulse times from the first path and the amplitudes from the second path to obtain the timing and amplitude of the stimulation pulses to be applied to the recipient of the medical device.

Embodiments of the present invention are described herein primarily in connection with one type of hearing prosthesis, namely cochlear implants. Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear.

FIG. 1 is a perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119, and is implanted into cochlea 140. In some embodiments electrode assembly 118 may be implanted at least in basal region 116, and sometimes further. For example, electrode assembly 118 may extend towards apical end of cochlea 140, referred to as cochlear apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrodes 148 to cochlea 140, thereby stimulating auditory nerve 114.

Because the cochlea is tonotopically mapped, that is, partitioned into regions each responsive to stimulus signals in a particular frequency range, each electrode of the implantable electrode array delivers a stimulating signal to a particular region of the cochlea. In the conversion of sound to electrical stimulation, frequencies are allocated to individual electrodes of the electrode assembly that lie in positions in the cochlea that are close to the region that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations. In achieving this, processing channels of the sound processing unit 126, that is, specific frequency bands with their associated signal processing paths, are mapped to a set of one or more electrodes to stimulate a desired nerve fiber or nerve region of the cochlea. Such sets of one or more electrodes for use in stimulation are referred to herein as "electrode channels" or "stimulation channels."

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

The cochlear implant 100 of FIG. 1 may be used in bilateral implant systems. For example, in embodiments, a cochlear implant 100 may be fitted to both the right ear and left ear of a recipient to form a bilateral implant system. These cochlear implants in such a bilateral system may operate independently of one another, or, for example, may communicate either wireless or via a wired connection in delivering joint stimulation to the recipient.

Figure 2:
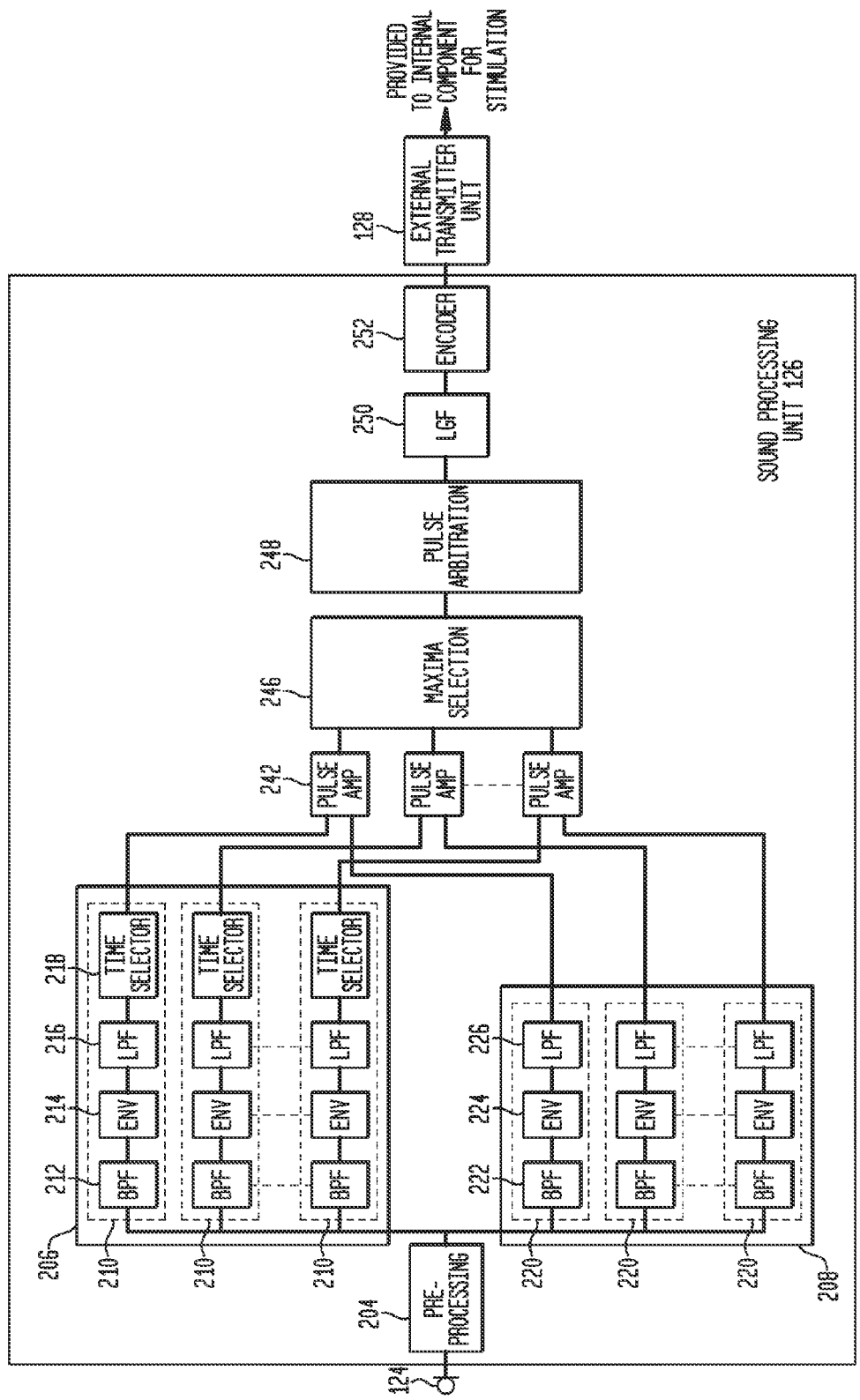
FIG. 2 illustrates a functional diagram of an exemplary sound processing unit, in accordance with an embodiment.

FIG. 2 illustrates a functional diagram of an exemplary sound processing unit 126, in accordance with an embodiment. As illustrated, sound processing unit 126 receives input from one or more sound input devices, such as microphone 124. It should be appreciated, however, that any sound input device now or later developed may be used to provide one or more input sound signals. For example, in an embodiment, the sound input device may be, for example, an input jack for receiving a signal from, for example, the headphone jack of an MP3 player or other audio device.

This input is provided to a pre-processor 204. Pre-processor 204 may, for example, use a pre-emphasis filter, automatic gain control (AGC), and/or manual sensitivity control (MSC), and other signal pre-processing components. The structure and operation of audio-preprocessor 204 is considered to be well-known in the art and, therefore, is not described further herein.

After which, the signal is provided to two separate paths: a timing path 206 and a spectral path 208. The timing path 206 determines the timing of the pulses for the stimulation channels, and the spectral path 208 provides the intensity of the stimulation for each pulse. As illustrated, timing path 206 comprises a plurality of different timing channels 210, one corresponding to each stimulation channel for the cochlear implant. Each timing channel 210 comprises a band-pass filter 212, an envelope detector 214, a low-pass filter 216, and a pulse time selector 218. Similarly, the spectral path 208 likewise comprises a plurality of channels 220 each corresponding to a particular stimulation channel, and each spectral channel 220 comprises a band-pass filter 222, an envelope detector 224, and a low-pass filter 226. The operation of each of these paths will be discussed in further detail below with regard to FIG. 3.

The outputs from each corresponding channel of timing path 206 and spectral path 208 are provided to a corresponding pulse amplitude combiner 242, which combines the pulse times from the timing path 206 with corresponding amplitudes from the spectral path 208. The pulse times and amplitudes may then be provided to an optional maxima selector 246, which may select a number of maxima from the received pulse times and amplitudes. These maxima may then be provided to a pulse arbitrator 248 that resolves any conflicts between the determined maxima to provide of output stimulation signals. The output stimulation signals may then be provided to a loudness growth function 250, followed by an encoder 252. After which, the encoded stimulation signals may be provided to the external transmitter unit 128 for transmission to the internal component of the cochlear implant where the stimulation may be applied to the recipient via the electrode array. The operation of each of these components will be discussed in more detail below with regard to FIG. 3.

Figure 3:
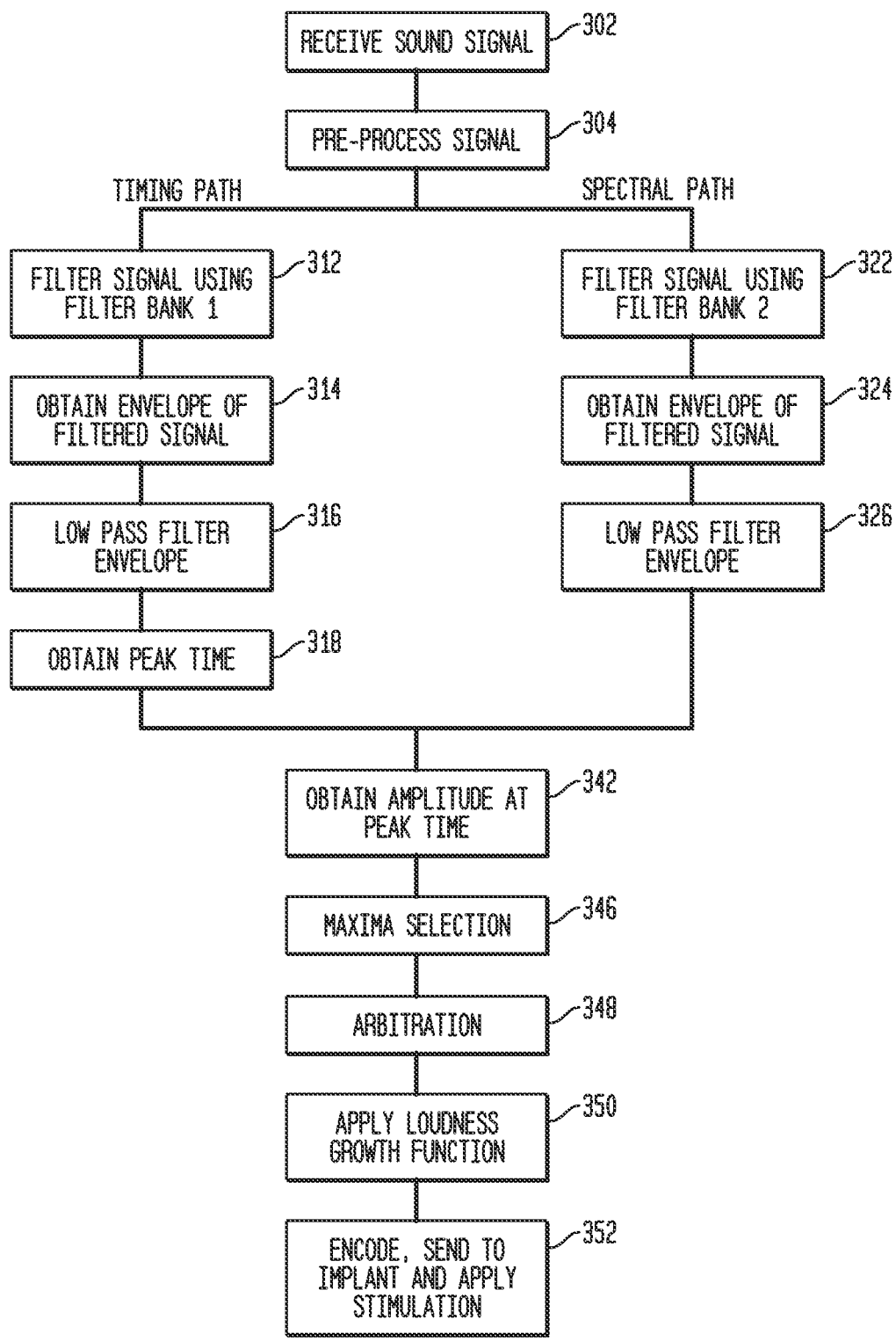
FIG. 3 illustrates and exemplary flow chart for obtaining pulse times and corresponding amplitudes for stimulation signals, in accordance with an embodiment.

FIG. 3 illustrates an exemplary flow chart for obtaining pulse times and corresponding amplitudes for stimulation signals to be applied to a recipient. FIG. 3 will be discussed with reference to the above-described FIG. 2. At block 302, sound processing unit 200 may receive an input sound signal from at least one sound input device, such as microphone 124. Sound input device 124 then provides the received audio signal to preprocessor 204 at block 304. Preprocessor 204 provides output signals to two separate signal paths: timing path 206 and spectral path 208. Each path 206 and 208 preferably filters, at blocks 312 and 322, respectively, the received signals using a bank of band-pass filters 212 and 222, respectively, to obtain a plurality of signals. The filter banks may provide a signal for each of the stimulation channels of hearing implant. For example, each filter bank may comprise N band-pass filters 212 and 222, where N is the number of stimulation channels for the cochlear implant. For example, for an implant system providing 22 channels of stimulation, each filter bank may include 22 separate band-pass filters, one for each stimulation channel, and output 22 separate signals.

The bandwidth of each band-pass filter 212 and 222 filter may be as narrow as the frequency spacing between channels or as wide as passing the entire signal (i.e. no filter). In embodiments, the bandwidths of the band-pass filters 212 of the timing path 206 may be kept relatively wide (e.g., a bandwidth of >300 Hz) in order to increase the likelihood of the channel containing several unresolved harmonics that may result in larger amplitude envelope fluctuations in the channel at the fundamental frequency. For example, if the fundamental frequency is 100 Hz for a received speech sound signal, then there may be harmonics located every 100 Hz above the fundamental frequency (i.e., harmonics located at frequency 200 Hz, 300 Hz, 400 Hz, etc.) If a band-pass filter 212 in the filter bank has a center frequency of 1000 Hz (or 1 kHz) and a bandwidth of 500 Hz, then the band-pass filter will pass the following 5 harmonics: 800 Hz, 900 Hz, 1000 Hz, 1100 Hz, and 1200 Hz. In contrast, if the band-pass filter has a bandwidth of only 50 Hz, then the filter will only pass the harmonic of 1000 Hz. Further, in an embodiment employing 22 stimulation channels, the bandwidth of each band-pass filter may be set to 2 times the filter spacing (i.e., the difference in frequencies between the center frequencies of adjacent band-pass filters), thus creating a largely overlapping filter bank. The band-pass filters 212 may be any type of filter, such as, for example, a finite impulse response (FIR) or infinite impulse response (IIR) filter. Further, in embodiments, a fast fourier transform (FFT) filterbank may be used to implement the filters 212.

Each band-pass filter 212 may then output the filtered signal to an envelope detector 214 at block 314. The envelope detector 214 may be a relatively wideband envelope detector, such as, for example, a Hilbert envelope detector. The envelope detector 214 may be followed by an low-pass filter 216 set to a cut-off frequency (e.g. 300-600 Hz) that limits the stimulation rate in that channel at block 316. This combination of envelope detection and low-pass filtering may help limit the stimulation rate in each channel so that the stimulation rate is limited to a rate within the perceptually-relevant range of the recipient (e.g., less than 300 Hz, although this number may vary by recipient). As used herein the term "perceptually relevant" refers to a characteristic or parameter that can be perceived by a recipient other than loudness. For example, timing pulse rates are considered perceptually relevant if the timing differences between pulse rates can effect some different perception by the recipient other than loudness. In the present description the perceptually relevant range generally refers to pulse rate frequencies of less than 300-600 Hz.

A pulse time selector 218 may follow the low pass filter 216 that finds the temporal locations of amplitude peaks in the envelope time waveform at block 318. These times may be used as the pulse times for corresponding stimulation channel. It should be noted that although in this embodiment, the peaks are selected as the pulse times, in other embodiments other phases of the waveform may be selected as the pulse times. For example, the troughs (i.e., minimum values) may be selected as the peak times, or the zero-crossing when the signal is rising or falling, etc. By selecting the timing of the stimulation pulses based on a particular phase of the temporal envelope, the present embodiment may help to more faithfully represent the fundamental frequency and interaural timing cues.

The second processing path, or "spectral" path 208, may be used to determine the amplitude of each stimulation pulse determined by the timing path. The spectral path may also comprise N band-pass filters 222, each corresponding to a particular stimulation channel for the cochlear implant. The filters 222 filter the received signal to generate a resulting signal at block 322. An envelope detector 224 may then detect the envelope for the resulting signal at block 324, which is then filtered at block 326 by low pass filter 226. In an embodiment, the center frequency of each band-pass filter 222 may be the same as that in the timing path (i.e., the corresponding band-pass filter 212). Further, the bandwidth of each filter 222 (e.g., as determined from the −3 dB points) may match the filter spacing of filters 222, thus creating a filter bank in the spectral path 208 with contiguous frequency boundaries. Additionally, in an embodiment, the low pass filters 226 of the spectral path may have a lower-cutoff frequency (e.g., 50 Hz) than in the timing path.

The corresponding channels from the timing and spectral paths may be consolidated at block 342 by a pulse amplitude combiner 242. For example, the pulse amplitude combiner 242 may receive the pulse times for the corresponding stimulation channel from the timing path 206 and then obtain the amplitude of the envelope from the spectral path 208 for the corresponding time and channel. The combiner 242 may then set the pulse amplitude for the stimulation to be applied as equal to this obtained amplitude.

FIG. 4 illustrates an exemplary timing signal 402 for a particular channel received from the timing path 206 along with an exemplary spectral signal 404 received from the spectral path for the corresponding channel. These exemplary signals 402 and 404 may be, for example, signals resulting for the first syllable in the Mandarin phrase "ni hao." Further, in this example, the low pass filter 216 of the timing channel has a cut-off frequency of 300 Hz and the low-pass filter 226 for the spectral path has a cut-off frequency of 50 Hz. FIG. 5 illustrates exemplary combined output pulses 502 resulting from the corresponding combiner 242 combining the pulse times from the timing path (i.e., the time corresponding to the peaks for signal 402) with the amplitudes from the corresponding envelope from the spectral path (i.e., signal 404). FIG. 6 illustrates the instantaneous pulse rate 602 of the output pulses 502 of FIG. 5. As illustrates, the pulse rate 602 increases as the fundamental frequency increases (e.g., the upward tone in the Mandarin phrase). It should be noted that in FIG. 6 the determination of the instantaneous pulse rate 602 becomes noisy after about 0.45 seconds due to the low and likely imperceptible pulse amplitudes after about 0.45 seconds as illustrated in FIG. 5. FIG. 7 illustrates a close-up view of the period between 0.3 and 0.4 seconds of the timing signal 402, the spectral signal 404, and the resulting output pulses 502.

The combined pulse times and amplitudes for the stimulation channels may then be passed to an optional maxima selection stage 246 at block 346. Maxima selection stage 246 selects channels for stimulation during a given time frame based on, for example, a particular stimulation strategy. For example, in an embodiment, the strategy for maxima selection may be based on a simple rule that eliminates channels with the smallest amplitude pulses or, for example, a more sophisticated rule, such as one based on psychophysical masking or channel-interaction minimization.

Next, the pulses selected by the maxima selection stage 246 (i.e., the selected maxima) are sent to an optional pulse arbitrator 248 at block 348. The arbitrator 248 may deal with temporally overlapping pulses by giving priority to pulses with the highest amplitude and delaying, for example, or dropping smaller-amplitude pulses. Finally, the remaining pulses are converted from acoustical units to the appropriate current levels via, for example, a loudness growth function 250 at block 350. It should be noted that in embodiments, a pulse arbitrator 248 may be included but not a maxima selection stage 246, or a maxima selection stage 246 may be included but not a pulse arbitrator 248, or, for example, neither a pulse arbitrator 248 nor maxima selection stage 246 included.

At block 352, the resulting signals may then be provided to an encoder 252 that encodes the signals for transmission from the sound processing unit to the internal component for application of the stimulation to the recipient. There are several speech coding strategies that may be used when converting sound into all electrical stimulation signals. Embodiments of the present invention may be used, for example, on a subset of the stimulation channels in combination with a variety of speech strategies on the remaining stimulation channels including but not limited to Continuous Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HIRES™ (HIRES is a trademark of Advanced Bionics), developed by Advanced Bionics. SPEAK is a low rate strategy that may operate within the 250-500 Hz range. ACE is a combination of CIS and SPEAK.

The encoded stimulation signals may then be transmitted to the internal component 144 via the external transmitter unit 128. The signals may then be received by the internal receiver unit 132 and provided to the stimulation unit 120 that may determine, based on the stimulation strategy being implemented, information and signals for use in applying stimulus via the electrode array 142. For example, stimulus controller 208 may select for each of the received stimulation signals the electrode(s) to be used as well as the specific amount of current to apply to each electrode to achieve the specified stimulation amplitude. The stimulation unit 102 may further implement a particular mode of stimulation, such as, for example, bi-polar or mono-polar.

The latency of the cochlear implant system may be fixed (i.e., the time it takes for a received sound signal to be processed and provided to the recipient may be a fixed period of time) in certain embodiments. Thus, in embodiments of bi-lateral cochlear systems, the subtle phase differences between sound signals received at the left and right ears may be maintained when presenting the resulting stimulation to the recipient. In other words, in embodiments, because the latency in the cochlear implants is fixed, the slight differences in time between when a sound signal arrives at the left ear versus the right ear may be maintained such that independent cochlear implants for the left and right ears may each deliver the resulting stimulation signal from the sound with the same time difference between when the two independent cochlear implant systems received the sound.

In bi-lateral cochlear implant systems, limiting the stimulation rate to a rate within the perceptually-relevant range may help to maintain the timing of the acoustic waveform and thus with binaural sensitivity in the recipient to interaural timing differences (ITD). Additionally, because in embodiments the timing of the pulses is variable and within the perceptually-relevant range of the recipient, the frequency of the stimulations pulses may be lower without unduly suffering from sounding too robotic. That is, in embodiments, the delivered stimulation may be perceived by the recipient as more natural sounding with a lower stimulation pulse rate. Additionally, because the frequency of the pulses is lower, the number of delivered stimulation pulses is reduced. This may help reduce the power requirements of the cochlear implant system, and thus improve battery life and/or allow for the use of smaller more affordable batteries.

It should be noted that the above-described embodiment of FIG. 2 was merely one exemplary embodiment provided for illustrative purposes, and is not restrictive on the invention as claimed. For example, in another embodiment, corresponding band-pass filters 212 and 222 in the timing path 206 and spectral path 208 may have identical filter cut-off frequencies. Or, for example, the timing path 206 and spectral path 208 may use common band-pass filters and the signals split off into the two different paths after the passing through the common filter bank (i.e., band-pass filters 212 and 222 are combined into a single band-pass filter). Or, in yet another example, the timing path 206 and spectral path 208 may use common band-pass filters, envelope detectors, and/or low-pass filters. In an embodiment in which both paths use common band-pass filters, envelope detectors and low-pass filters, the signals may be split out after passing through the bank of low-pass filters.

In yet other embodiments, the timing path may use a reduced number of timing channels as opposed to a single timing channel for each stimulation channel of the cochlear implant. For example, in an embodiment, each timing channel may be used to determine pulses for one or multiple stimulation channels, such as, for example, a single timing channel may be used to initiate pulses for all spectral channels. In such a scenario, all channels would receive simultaneous pulse times, but the arbitration stage could stagger pulses along the cochlea from basal-to-apical or apical-to-basal. Further, if such staggering is used, then a fixed delay may be assigned to each channel in order to maintain consistent within-channel timing.

While the embodiment of FIG. 2 uses amplitude peaks of the temporal envelope for timing, other methods and systems may be used to derive the pulse times for the different stimulation channels. For example, in an embodiment, the DC component of the envelope may be removed (e.g., by a high-pass filter) and then zeros-crossings detected (e.g., positive or negative zero-crossings). The times of these zero-crossings may then be used as the pulse times for the stimulation channels. In such an example, either the positive going zero-crossings or negative zero-crossings may be used to determine the pulse times, or even, for example, a combination thereof or both positive and negative zero-crossings may be used. Additional methods exist to extract the instantaneous phase of the timing paths temporal envelope (e.g. by applying a Hilbert transform to the temporal envelope). If instantaneous phase is derived, then the envelope timing may be determined by choosing to simulate at a given instantaneous phase of the envelope (e.g., the zero-crossings when the signal is rising, the zero-crossings when the signal is falling, etc.).

In the above-discussed embodiment of FIG. 2, low-pass filtering using low pass filters 216 follows envelope detection in order to help limit the maximum frequency in the temporal envelope. It should be noted that these low pass filters 216 and 226 are optional. For example, in other embodiments, other methods and systems may be used to help limit the maximum frequency of the temporal envelope. For example, in an embodiment, the bandwidth of the band-pass signal before envelope detection may be limited to help limit the maximum frequency of the Hilbert/quadrature envelope. Or, for example, envelope detectors 241 may use a type of envelope detection (e.g. half-wave rectification followed by lowpass filtering that has a low-pass filtering built in.

In particular, various implementations of the subject matter described, such as the embodiment of FIG. 2, components may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method, comprising:
    filtering a received signal to obtain a set of band-pass filtered signals;
    determining one or more envelopes for at least one of the band-pass filtered signals;
    determining, for at least one envelope of the one or more envelopes, a pulse rate for stimulation pulses at a corresponding stimulation channel of a stimulating medical device, wherein the pulse rate is based on when a detected value of a characteristic of the at least one envelope is equal to a specified value of the characteristic; and
    delivering stimulation pulses via the corresponding stimulation channel using the pulse rate.

2. The method of claim 1, further comprising:
    determining, based on at least one of the one or more envelopes, one or more pulse amplitudes for stimulation pulses at the corresponding stimulation channel; and
    delivering stimulation pulses via the corresponding stimulation channel using the pulse rate and the one or more pulse amplitudes.

3. The method of claim 1, wherein each stimulation channel corresponds to one or more electrodes for use in delivering stimulation pulses.

4. The method of claim 1, wherein the set of band-pass filtered signals includes a plurality of band-pass filtered signals each corresponding to one of a plurality of stimulation channels of the stimulating medical device, and further comprising:
    determining a plurality of envelopes, wherein each of the plurality of envelopes corresponds to one of the plurality of band-pass filtered signals;
    determining pulse rates for stimulation pulses on stimulation channels corresponding to the plurality of band-pass filtered signals based on when a detected value of a characteristic of the corresponding envelope is equal to a specified value of the characteristic; and
    delivering, via the stimulation channels corresponding to the plurality of band-pass filtered signals, stimulation pulses using the corresponding pulse rate.

5. The method of claim 1, further comprising:
    determining, based on at least one of the one or more envelopes for each of the plurality of band-pass filtered signals, one or more pulse amplitudes for stimulation pulses at the corresponding stimulation channels; and
    delivering, via the stimulation channels corresponding to the plurality of band-pass filtered signals, stimulation pulses using the corresponding pulse rate and one or more pulse amplitudes.

6. The method of claim 5, further comprising:
    selecting a plurality of maxima from the pulse amplitudes; and
    arbitrating between the selected maxima to determine a set of stimulation pulse rates and corresponding pulse amplitudes for use in delivery of stimulation pulses to the recipient.

7. The method of claim 6, wherein arbitrating between the selected maxima comprises:
    selecting a set of stimulation pulses with the highest amplitude and at least one of delaying or dropping stimulating pulses having smaller amplitudes.

8. The method of claim 1, wherein the characteristic of the envelope is amplitude and the specified value is equal to a maximum value of the amplitude.

9. The method of claim 1, further comprising:
    high-pass filtering the one or more envelopes to remove DC components of the one or more envelopes; and
    detecting zero-crossings of the one or more high-pass filtered envelopes,
    wherein the characteristic of the envelope is one or more of the detected zero crossings.

10. The method of claim 9, wherein the characteristic of the envelope is one of only positive going zero-crossings, only negative going zero-crossings, or a combination of positive going and negative going zero-crossings.

11. The method of claim 1, further comprising:
    extracting an instantaneous phase of the one or more envelopes,
    wherein the characteristic of the envelope is one or more selected instantaneous phases.

12. The method of claim 1, further comprising:
low-pass filtering each of the one or more envelopes, wherein the pulse rate of stimulation pulses is limited by a cutoff frequency of the corresponding low-pass-filtering.

13. The method of claim 12, wherein the low-pass filtering includes:
setting the cutoff frequency so as to limit low-pass filtered envelopes to a frequency range for which a parameter other than loudness can be perceived by a recipient of the stimulating medical device.

14. The method of claim 1, further comprising:
encoding the stimulation pulses using different speech coding strategies at different subsets of the stimulation channels.

15. The method of claim 14, wherein the different speech coding strategies are selected from a group comprising a Continuous Interleaved Sampling (CIS) strategy, a Spectral PEAK Extraction (SPEAK) strategy, and an Advanced Combination Encoders (ACE) strategy.

* * * * *